(12) United States Patent
Takata et al.

(10) Patent No.: US 12,649,068 B2
(45) Date of Patent: Jun. 9, 2026

(54) LIGHT IRRADIATING MEDICAL DEVICE

(71) Applicant: KANEKA CORPORATION, Osaka (JP)

(72) Inventors: Hironori Takata, Settsu (JP); Akio Fujii, Settsu (JP)

(73) Assignee: KANEKA CORPORATION, Osaka (JP)

( * ) Notice: Subject to any disclaimer, the term of this patent is extended or adjusted under 35 U.S.C. 154(b) by 989 days.

(21) Appl. No.: 17/630,405

(22) PCT Filed: Jul. 16, 2020

(86) PCT No.: PCT/JP2020/027627
§ 371 (c)(1),
(2) Date: Jan. 26, 2022

(87) PCT Pub. No.: WO2021/033465
PCT Pub. Date: Feb. 25, 2021

(65) Prior Publication Data
US 2022/0288410 A1     Sep. 15, 2022

(30) Foreign Application Priority Data

Aug. 20, 2019     (JP) ................................. 2019-150239

(51) Int. Cl.
*A61N 5/06* (2006.01)
*A61B 18/22* (2006.01)
(Continued)

(52) U.S. Cl.
CPC .... *A61N 5/0601* (2013.01); *A61B 2018/2261* (2013.01); *A61B 2090/3966* (2016.02);
(Continued)

(58) Field of Classification Search
CPC ............ A61N 5/0601; A61N 2005/063; A61N 5/062; A61N 5/0603; A61N 2005/0602;
(Continued)

(56) References Cited

U.S. PATENT DOCUMENTS

| | | | |
|---|---|---|---|
| 6,013,053 A | 1/2000 | Bower et al. | |
| 6,086,558 A | 7/2000 | Bower et al. | |

(Continued)

FOREIGN PATENT DOCUMENTS

| | | |
|---|---|---|
| JP | 2001-505443 A | 4/2001 |
| JP | 2007-521890 A | 8/2007 |
| JP | 2015-77168 A | 4/2015 |

OTHER PUBLICATIONS

International Search Report for PCT/JP2020/027627 mailed on Oct. 6, 2020.
(Continued)

*Primary Examiner* — Allen Porter
*Assistant Examiner* — Moussa Haddad
(74) *Attorney, Agent, or Firm* — Birch, Stewart, Kolasch & Birch, LLP

(57) ABSTRACT

A light irradiating medical device comprising: a shaft extending in a longitudinal axis direction thereof and having a lumen extending in the longitudinal axis direction; a first tubular member disposed in the lumen of the shaft and rotatable about a rotation axis parallel to the longitudinal axis direction of the shaft, the first tubular member having a window located in a part of a peripheral wall of a distal portion; and a light guiding tool disposed in a lumen of the first tubular member and movable in the longitudinal axis direction, the light guiding tool including an optical fiber extending in the longitudinal axis direction, the optical fiber including a core, a cladding coating a radially outer portion of the core, and a cladding-absent portion located at a part
(Continued)

of a distal portion of the core, and the window allowing passage therethrough of output light from the light guiding tool.

16 Claims, 8 Drawing Sheets

(51) Int. Cl.
*A61B 90/00* (2016.01)
*A61M 25/10* (2013.01)

(52) U.S. Cl.
CPC .............. *A61M 25/10* (2013.01); *A61N 5/062* (2013.01); *A61N 2005/063* (2013.01); *A61N 2005/0632* (2013.01)

(58) Field of Classification Search
CPC .... A61N 2005/0609; A61N 2005/0608; A61N 2005/0632; A61N 2005/0664; A61B 18/22; A61B 2018/00196; A61B 2018/0022; A61B 2018/00345; A61B 2018/00482; A61B 2018/00577; A61B 2018/2261; A61B 2018/2285; A61B 2090/376; A61B 2090/3966; A61M 25/04; A61M 25/10
See application file for complete search history.

(56) References Cited

U.S. PATENT DOCUMENTS

| 10,631,930 | B1 * | 4/2020 | Miyagawa ............. A61B 18/24 |
| 2006/0093276 | A1 * | 5/2006 | Bouma ............... A61B 1/3137 |
| | | | 385/72 |
| 2008/0071331 | A1 | 3/2008 | Rubinchik et al. |
| 2014/0088571 | A1 * | 3/2014 | Loeb ...................... A61B 18/24 |
| | | | 606/3 |
| 2020/0289202 | A1 | 9/2020 | Miyagawa et al. |
| 2022/0011506 | A1 * | 1/2022 | Seifert ............... C03B 37/0122 |
| 2022/0047885 | A1 * | 2/2022 | Tsukamoto ........... A61B 90/39 |

OTHER PUBLICATIONS

Written Opinion of the International Searching Authority for PCT/JP2020/027627 (PCT/ISA/237) mailed on Oct. 6, 2020.

* cited by examiner

[FIG. 1]
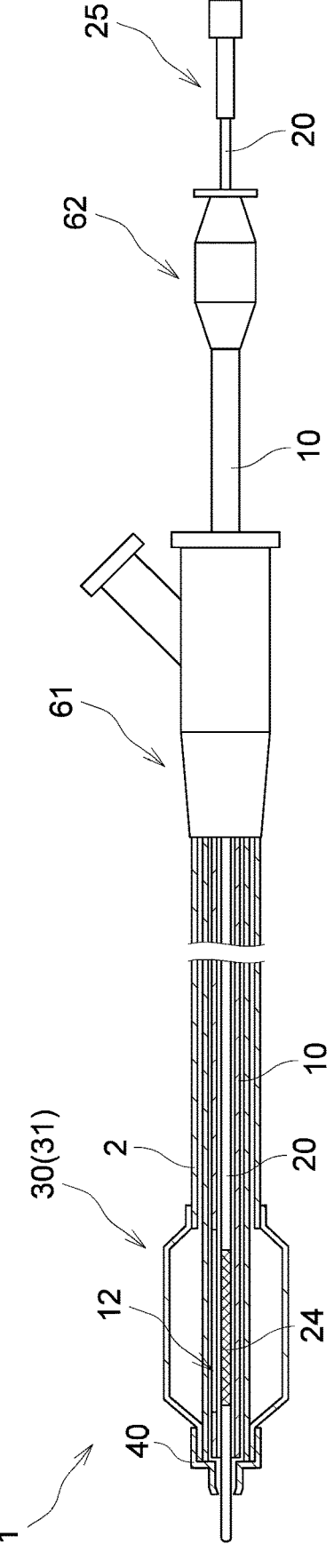

[FIG. 2]
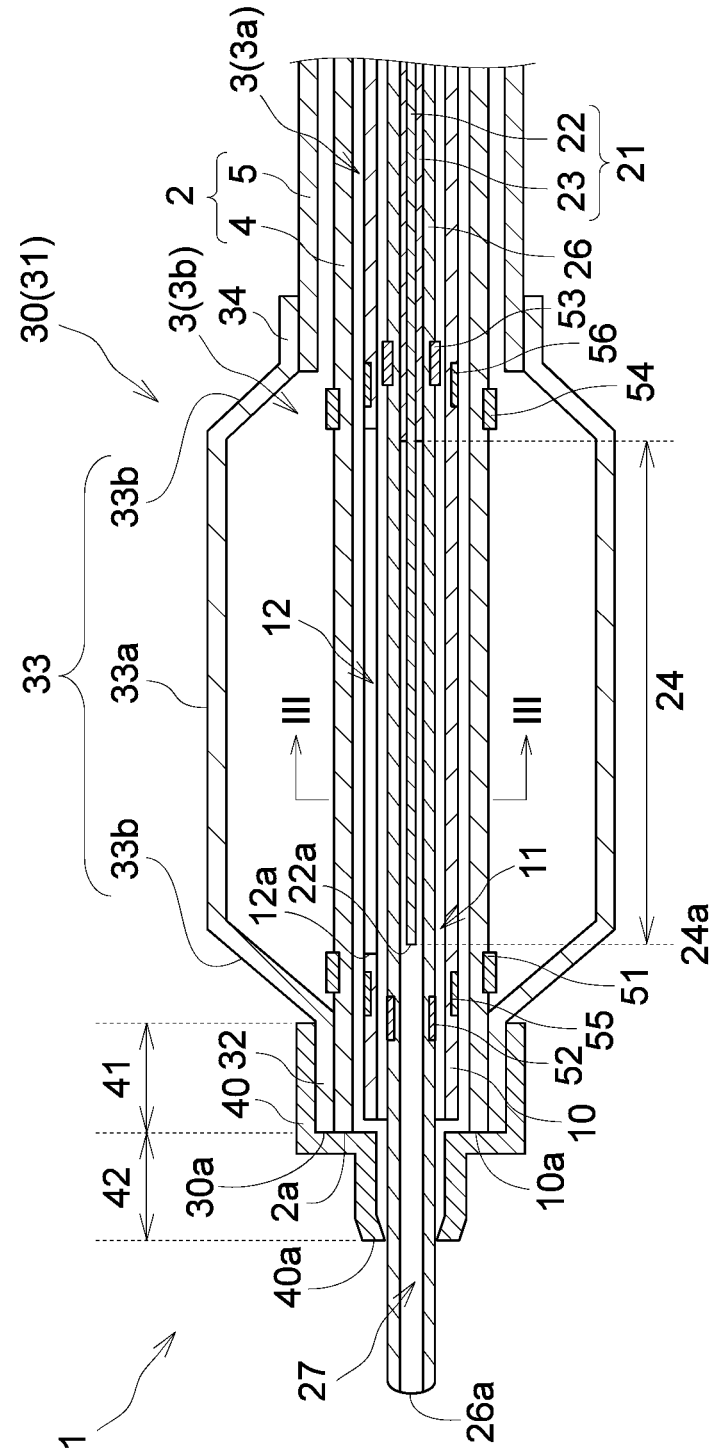

【FIG. 3】
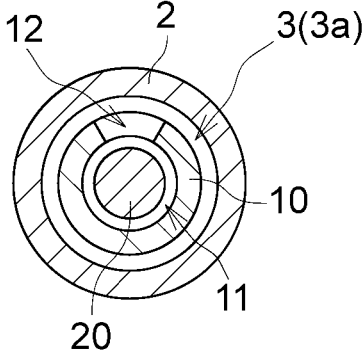

【FIG. 4】
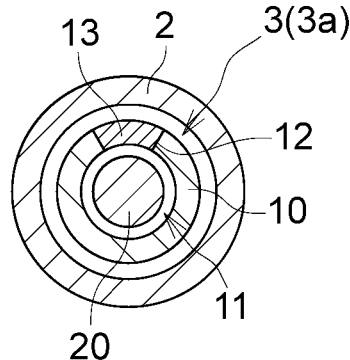

【FIG. 5】
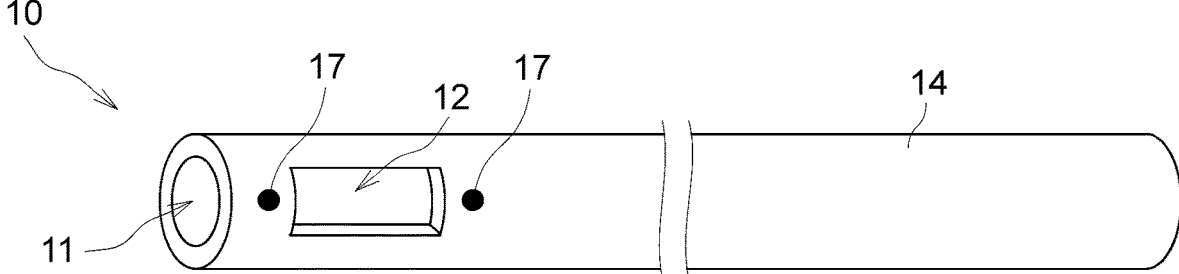

【FIG. 6】
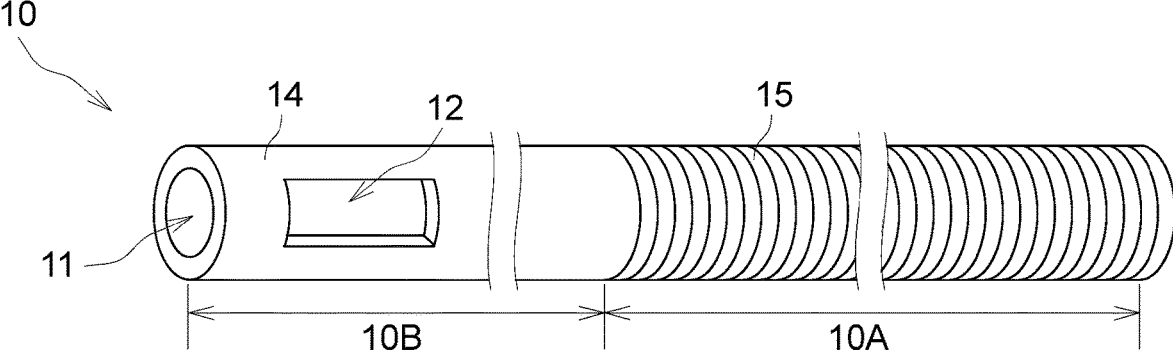

【FIG. 7】
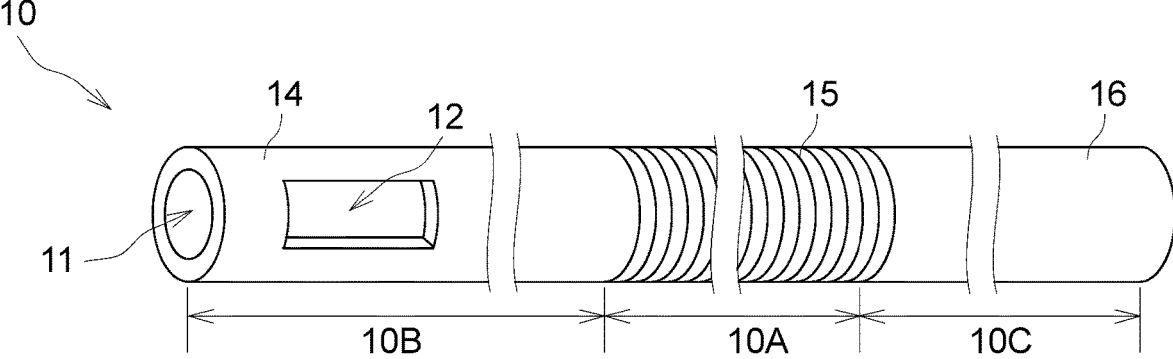

[FIG. 8]
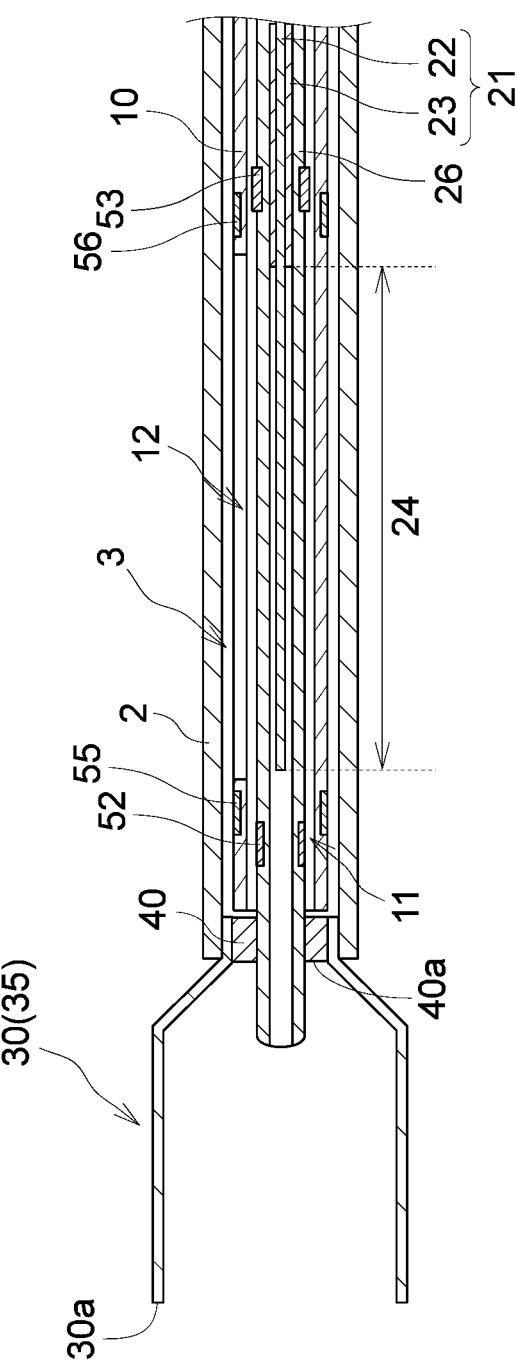

LIGHT IRRADIATING MEDICAL DEVICE

TECHNICAL FIELD

The present invention relates to a light irradiating medical device for irradiating a tissue of cancer cells or the like with light in a lumen in the body such as a blood vessel or a gastrointestinal tract.

BACKGROUND ART

In photodynamic therapy (PDT), a photosensitizer is administered into the body by means of intravenous injection or intraperitoneal administration, accumulates in a target tissue of cancer cells or the like, and is irradiated with a light having a specific wavelength so that the photosensitizer is excited. When the state of the excited photosensitizer returns to a ground state, energy conversion occurs so that reactive oxygen species are generated. The reactive oxygen species attack the target tissue, whereby the target tissue can be eliminated. Meanwhile, in ablation (tissue cauterization) using laser light, a target tissue is irradiated with laser light to be cauterized.

In a light irradiating medical device used for PDT or optical ablation, an optical fiber is disposed inside a catheter tube in order to irradiate a target tissue with light.

Patent Literature 1 discloses a device that supplies irradiation light to a predetermined region and that includes a balloon catheter having a delimited treatment window. The device includes a center channel and an exterior sleeve. The center channel is a transparent channel into which an optical fiber probe can be inserted. The exterior sleeve is used for balloon inflation and has a proximal end and a distal end. The exterior sleeve further includes an inflatable balloon near the distal end. The balloon is, at each of both end portions thereof, coated with a reflection material for delimiting the treatment window.

Patent Literature 2 discloses an ablation device including: a shaft; a balloon; a first lumen; a second lumen; a light guiding material; a diffusion member; and a tubular member. The balloon is provided at the distal end side of the above shaft and is elastically inflatable. The first lumen is formed along the above shaft and allows a fluid to flow therethrough into the above balloon. The second lumen is formed along the above shaft and allows a fluid to flow out therethrough from the above balloon. The light guiding material is provided along the above shaft and guides laser light into the above balloon. The diffusion member reflects or diffuses, in a direction intersecting with a first direction in which the above light guiding material extends, laser light outputted from the above light guiding material inside the above balloon. The tubular member is provided inside the above balloon so as to enclose the above diffusion member. The tubular member has, on the inner surface side thereof, a reflection layer that reflects or blocks the laser light reflected or diffused by the above diffusion member. The tubular member has a transmission window allowing transmission therethrough of the laser light to outside of the reflection layer.

Patent Literature 3 discloses administering a photosensitive substance by using a delivery device in photodynamic therapy for treating a prostatic disorder. The delivery device includes a channel in which a guide wire is received so as to be able to be inserted therethrough. Activation energy is delivered by using an irradiation device including: an energy source; and a channel in which a guide wire is received so as to be able to be inserted therethrough. The guide wire is used for positioning the delivery device and/or the irradiation device. In addition, Patent Literature 3 further indicates that the irradiation device can be slid, i.e., rotated, in a side-surface direction while extending along the guide wire.

PRIOR ART DOCUMENTS

Patent Documents

Patent Document 1: JP 2001-505443 A
Patent Document 2: JP 2015-77168 A
Patent Document 3: JP 2007-521890 A

SUMMARY OF THE INVENTION

Problems to be Solved by the Invention

However, in the device disclosed in the above Patent Literature 1, the position for irradiation with light is determined by the treatment window provided to the balloon. Thus, in order to change the position for irradiation after the balloon is expanded to be fixed to the inside of the body, the catheter needs to be moved to the distal side or the proximal side or needs to be rotated in a state where the balloon is contracted. Consequently, the treatment is complicated. In addition, in the device disclosed in Patent Literature 2, the position for irradiation with light is determined by the transmission window provided to the tubular member connected to the light guiding material (optical fiber). Thus, in order to adjust the position for irradiation, the light guiding material needs to be moved to the distal side or the proximal side or needs to be rotated. Consequently, the light guiding material may be damaged by this motion. Further, the irradiation device disclosed in Patent Literature 3 can also be rotated, and thus the irradiation device may be damaged. Considering these problems, an object of the present invention is to provide a light irradiating medical device capable of adjusting the position for irradiation with output light while preventing damage to a light guiding tool.

Solutions to the Problems

One embodiment of a light irradiating medical device of the present invention that has achieved the above purposes comprising: a shaft having a first end and a second end in a longitudinal axis direction thereof and having a lumen extending in the longitudinal axis direction; a first tubular member disposed in the lumen of the shaft and rotatable about a rotation axis parallel to the longitudinal axis direction of the shaft, the first tubular member having a window located in a part of a peripheral wall of a distal portion; and a light guiding tool disposed in a lumen of the first tubular member and movable in the longitudinal axis direction, the light guiding tool including an optical fiber extending in the longitudinal axis direction, the optical fiber including a core, a cladding coating a radially outer portion of the core, and a cladding-absent portion located at a part of a distal portion of the core, and the window allowing passage therethrough of output light from the light guiding tool.

The light irradiating medical device is preferable wherein the first tubular member is made from a material having a lower property of allowing passage therethrough of the output light than the window.

The light irradiating medical device is preferable wherein a transparent member disposed in the window, the transparent member allowing transmission therethrough of the output light.

The light irradiating medical device is preferable wherein a length of the window in the longitudinal axis direction of the shaft is larger than a length of the window in a circumferential direction of the shaft.

The light irradiating medical device is preferable wherein the window is located within a range of a length, in a circumferential direction of the shaft, that is one quarter of an entire circumference of the shaft.

The light irradiating medical device is preferable wherein an expansion portion disposed on a distal portion of the shaft and configured to expand radially outward of the shaft.

The light irradiating medical device is preferable wherein the expansion portion is: a balloon; a basket including a plurality of elastic wires; or a self-expandable-type stent.

The light irradiating medical device is preferable wherein the first tubular member has a first section provided with a reinforcing material containing a metal.

The light irradiating medical device is preferable wherein the first tubular member further has a second section located closer to a distal side than the first section is, the second section not being provided with the reinforcing material, and the window is located not in the first section but in the second section.

The light irradiating medical device is preferable wherein the first tubular member further has a third section located closer to a proximal side than the first section is, and the first tubular member is, at the third section, a pipe made from a metal.

The light irradiating medical device is preferable wherein a support portion disposed on a distal end portion of the shaft and supporting a distal portion of the light guiding tool.

The light irradiating medical device is preferable wherein the window is longer than the cladding-absent portion in the longitudinal axis direction of the shaft.

The light irradiating medical device is preferable wherein a reflection material disposed on an inner surface of the first tubular member and configured to refract, toward the window, output light from the core.

The light irradiating medical device is preferable wherein the light guiding tool includes a second tubular member covering the optical fiber and having light-transmitting property.

The light irradiating medical device is preferable wherein the first tubular member has, at a distal end portion thereof, a position indication portion indicating a position of the window.

The light irradiating medical device is preferable wherein the light guiding tool is not rotated, relative to the shaft, about an axis parallel to the longitudinal axis direction of the shaft.

Effects of the Invention

In the above light irradiating medical device, the window allowing passage therethrough of output light from the light guiding tool is formed in the first tubular member. Thus, the position for irradiation with light to be outputted to outside through the window can be adjusted in the circumferential direction or the longitudinal axis direction of the shaft by rotating the first tubular member or moving the first tubular member in the longitudinal axis direction of the shaft. Therefore, the position for irradiation with the output light can be adjusted without rotating the light guiding tool, whereby damage to the light guiding tool can be prevented.

BRIEF DESCRIPTION OF THE DRAWINGS

FIG. 1 shows a side view (partial cross-sectional view) of a light irradiating medical device according to one embodiment of the present invention.

FIG. 2 shows an enlarged cross-sectional view of a distal side of the light irradiating medical device shown in FIG. 1.

FIG. 3 shows a cross-sectional view, at III-III, of the light irradiating medical device shown in FIG. 2.

FIG. 4 shows a cross-sectional view of a modification of the device shown in FIG. 3.

FIG. 5 shows a perspective view of the first tubular member shown in FIG. 1.

FIG. 6 shows a perspective view of modifications of the first tubular member shown in FIG. 5.

FIG. 7 shows a perspective view of modifications of the first tubular member shown in FIG. 6.

FIG. 8 shows a cross-sectional view of a modification of the light irradiating medical device 1 shown in FIG. 2.

MODE FOR CARRYING OUT THE INVENTION

Hereinafter, the present invention will be more specifically described based on the following embodiments. However, the present invention is not limited to the following embodiments and, as a matter of course, can also be carried out with appropriate modifications being made within the scope of the gist described above and below, and any of these modifications are included in the technical scope of the present invention. In any of the drawings, hatching, reference characters for members, or the like may be omitted for convenience. In this case, see the description and the other drawings. Since priority is given to facilitating the understanding of the characteristics of the present invention, the dimensions of various members in the drawings may be different from actual dimensions.

A light irradiating medical device according to one aspect of the present invention has the following principal characteristics. That is, the light irradiating medical device includes: a shaft having a first end and a second end in a longitudinal axis direction thereof and having a lumen extending in the longitudinal axis direction; a first tubular member disposed in the lumen of the shaft and rotatable about a rotation axis parallel to the longitudinal axis direction of the shaft, the first tubular member having a window located in a part of a peripheral wall of a distal portion; and a light guiding tool disposed in a lumen of the first tubular member and movable in the longitudinal axis direction of the shaft. The light guiding tool includes an optical fiber extending in the longitudinal axis direction of the shaft. The optical fiber includes: a core; a cladding coating a radially outer portion of the core; and a cladding-absent portion located at a part of a distal portion of the core. The window allows passage therethrough of output light from the light guiding tool. In the above light irradiating medical device, the window allowing passage therethrough of output light from the light guiding tool is formed in the first tubular member. Thus, the position for irradiation with light to be outputted to outside through the window can be adjusted in a circumferential direction or the longitudinal axis direction of the shaft by rotating the first tubular member or moving the first tubular member in the longitudinal axis direction of the shaft. Therefore, the position for irradiation with the output light can be adjusted without rotating the light guiding tool, whereby damage to the light guiding tool can be prevented.

In PDT or optical ablation, the light irradiating medical device is used for irradiating, with a light having a specific wavelength, a treatment site which is a target tissue of cancer cells or the like in a lumen in the body such as a blood vessel or a gastrointestinal tract. The light irradiating medical device may be singly delivered to a treatment site or may be used together with a catheter and an endoscope for delivery. In treatment using an endoscope, the light irradiating medical device is disposed in the body and delivered to a treatment site through a forceps port for the endoscope. Hereinafter, the light irradiating medical device is sometimes referred to simply as an device.

A basic configuration of the light irradiating medical device will be described with reference to FIG. 1 to FIG. 3. FIG. 1 is a side view (partial cross-sectional view) of a light irradiating medical device according to one embodiment of the present invention. FIG. 2 is an enlarged cross-sectional view of a distal side of the light irradiating medical device shown in FIG. 1. FIG. 3 is a cross-sectional view, at III-III, of the light irradiating medical device shown in FIG. 2. A light irradiating medical device 1 includes a shaft 2, a first tubular member 10, and a light guiding tool 20.

In the present invention, the distal side of the light irradiating medical device 1 refers to a first end side in a longitudinal axis direction of the shaft 2, i.e., a treatment target side. A proximal side of the light irradiating medical device 1 refers to a second end side in the longitudinal axis direction of the shaft 2, i.e., the hand side of a user (operator). With each member being divided in a longitudinal axis direction thereof into two equal portions, the portion on the proximal side is sometimes referred to as a proximal portion and the portion on the distal side is sometimes referred to as a distal portion.

A material of each of the members composing the light irradiating medical device 1 desirably has biocompatibility.

The shaft 2 is a member having a first end and a second end in the longitudinal axis direction thereof and having a lumen 3 extending in the longitudinal axis direction. The first end may correspond to a distal end of the shaft 2, and the second end may correspond to a proximal end of the shaft 2. The shaft 2 has a tubular structure for disposing, in the lumen 3 thereof, the first tubular member 10 and the light guiding tool 20. Since the shaft 2 is inserted into a body, the shaft 2 preferably has flexibility.

The shaft 2 can be made from, for example: a synthetic resin such as a polyolefin resin (for example, polyethylene or polypropylene), a polyamide resin (for example, nylon), a polyester resin (for example, PET), an aromatic polyether ketone resin (for example, PEEK), a polyether polyamide resin, a polyurethane resin, a polyimide resin, or a fluorine resin (for example, PTFE, PFA, or ETFE); or a metal such as stainless steel, carbon steel, or nickel-titanium alloy. One type of these materials may be used alone, or two or more types of these materials may be used in combination.

The shaft 2 preferably contains a material having light transmitting property. Consequently, light is transmitted through the shaft 2. Thus, with the light guiding tool 20 (more preferably, a cladding-absent portion 24 of an optical fiber 21) being positioned inside the shaft 2, a target tissue can be efficiently irradiated with the light. Examples of the material having light transmitting property can include synthetic resins such as (meth)acrylic resins (for example, polymethyl methacrylate (PMMA)), polycarbonate resins (for example, poly(diethylene glycol bis(allyl carbonate)) (PC)), polystyrene-based resins (for example, methyl methacrylate-styrene copolymer resin (MS) and acrylonitrile styrene resin (SAN)), polyamide resins (for example, nylon), and polyolefin resins.

The shaft 2 preferably contains a material having light diffusing property. Consequently, light from the light guiding tool 20 is moderately diffused at the time of passage through the shaft 2. Thus, a target tissue can be evenly irradiated with the light. Examples of the material having light diffusing property include: inorganic-based particles such as particles of titanium oxide, particles of barium sulfate, and particles of calcium carbonate; and organic-based particles such as crosslinked acrylic-based particles and crosslinked styrene-based particles.

As shown in FIG. 1, a first handle 61 at which an operator grips the device 1 is preferably connected to the proximal portion of the shaft 2. If an expansion portion 30 described later is disposed on the distal portion of the shaft 2 and the expansion portion 30 is a balloon 31, a fluid supply tool such as a syringe for supplying a fluid into the balloon 31 through the lumen 3 of the shaft 2 may be connected to the first handle 61.

The first tubular member 10 is disposed in the lumen 3 of the shaft 2 and rotatable about a rotation axis parallel to the longitudinal axis direction of the shaft 2. A window 12 is located in a part of a peripheral wall of the distal portion of the first tubular member 10. The light guiding tool 20 is disposed in a lumen 11 of the first tubular member 10 and movable in the longitudinal axis direction of the shaft 2. The light guiding tool 20 has an optical fiber 21 extending in the longitudinal axis direction of the shaft 2. The optical fiber 21 includes: a core 22; a cladding 23 coating a radially outer portion of the core 22; and a cladding-absent portion 24 located at a part of the distal portion of the core 22. Output light from the light guiding tool 20 passes through the window 12. Since the window 12 allowing passage therethrough of output light from the light guiding tool 20 is formed in the first tubular member 10 in this manner, the position for irradiation with light to be outputted to outside through the window 12 can be adjusted in the circumferential direction or the longitudinal axis direction of the shaft 2 by rotating the first tubular member 10 or moving the first tubular member 10 in the longitudinal axis direction of the shaft 2. Therefore, the position for irradiation with the output light can be adjusted without rotating the light guiding tool 20, whereby damage to the light guiding tool 20 can be prevented.

A guide wire used for delivering the shaft 2 to a target tissue can be inserted through the lumen 11 of the first tubular member 10 before the light guiding tool 20 is inserted. Consequently, the light guiding tool 20 is easily moved in the longitudinal axis direction of the shaft 2 along the guide wire. The light irradiating medical device 1 may include a guide wire (not shown) extending in the longitudinal axis direction of the shaft 2. The guide wire can be pulled out before the light guiding tool 20 is inserted through the lumen 11 of the first tubular member 10, and the light guiding tool 20 can be disposed instead of the guide wire.

The optical fiber 21 of the light guiding tool 20 is a transmission path through which a light signal is transmitted to a target tissue. A connector 25 provided at a proximal end of the light guiding tool 20 is connected to a light source (not shown) such as a semiconductor laser. The optical fiber 21 includes: the core 22; the cladding 23 coating the radially outer portion of the core 22; and the cladding-absent portion 24 located at a part of the distal portion of the core 22. The materials forming the core 22 and the cladding 23 are not particularly limited, and plastic or a glass such as quartz glass or fluoride glass, can be used.

The cladding-absent portion 24 refers to a portion on which no cladding 23 is present at at least a part thereof in the circumferential direction of the core 22. The portion is a light output area of the optical fiber 21. Provision of such a cladding-absent portion 24 makes it possible to configure a light irradiating medical device 1 of a side surface irradiation type.

The position, in the longitudinal axis direction of the shaft 2, at which the cladding-absent portion 24 is provided is not particularly limited as long as the cladding-absent portion 24 is provided at a part of the distal portion of the core 22, but the cladding-absent portion 24 is preferably provided at a portion including a distal end 22a of the core 22. Consequently, the cladding-absent portion 24 is easily formed, and the flexibility of a distal end portion of the light guiding tool 20 can also be improved.

As shown in FIG. 2, the position of a distal end 24a of the cladding-absent portion 24 preferably coincides with the position of the distal end 22a of the core 22. Consequently, it is unnecessary to perform a difficult step of forming the cladding-absent portion 24 such that the cladding 23 remains at a portion including a distal end of the optical fiber 21. This can make it easy to perform a step of forming the light output area of the optical fiber 21.

The cladding-absent portion 24 can be formed by, for example, peeling the cladding 23 through etching or rubbing. It is more preferable to roughen the outer surface of the cladding-absent portion 24 by a method such as rasping. Consequently, the light diffusing property can be improved.

It is preferable that the light guiding tool 20 is not rotated, relative to the shaft 2, about an axis parallel to the longitudinal axis direction of the shaft 2. Consequently, the position for irradiation with light can be adjusted without rotating the optical fiber 21, whereby damage to the optical fiber 21 can be prevented.

The first tubular member 10 is formed in a tubular shape having the distal portion and the proximal portion. The first tubular member 10 can be provided with one or more lumens 11. However, in order to make the outer diameter of the first tubular member 10 small, the first tubular member 10 is preferably provided with only one lumen 11.

The first tubular member 10 can be made from, for example: a synthetic resin such as a polyolefin resin (for example, polyethylene or polypropylene), a polyamide resin (for example, nylon), a polyester resin (for example, PET), an aromatic polyether ketone resin (for example, PEEK), a polyether polyamide resin, a polyurethane resin, a polyimide resin, or a fluorine resin (for example, PTFE, PFA, or ETFE); or a metal such as stainless steel, carbon steel, or nickel-titanium alloy. One type of these materials may be used alone, or two or more types of these materials may be used in combination. The materials forming the shaft 2 and the first tubular member 10 may be the same as or different from each other.

The first tubular member 10 is preferably made from a material having a lower property of allowing passage therethrough of output light than the window 12. Consequently, output light is less likely to pass through an area other than a part of the peripheral wall of the distal portion of the first tubular member 10, i.e., a part at which the window 12 is formed. Thus, the position for irradiation with light to be outputted to outside through the window 12 can be adjusted in the circumferential direction or the longitudinal axis direction of the shaft 2. Examples of a configuration for setting the window 12 to have a higher property of allowing passage therethrough of output light than the first tubular member 10 in this manner include (i) a configuration in which the window 12 is opened and (ii) a configuration in which a transparent member 13 is disposed in the window 12.

As shown in FIG. 1 to FIG. 3, the window 12 may be opened, and the lumen 11 of the first tubular member 10 and the outside of the shaft 2 may be in communication with each other through the window 12. Consequently, the cladding-absent portion 24 of the light guiding tool 20 can be exposed to the outside from the window 12 of the first tubular member 10, whereby it becomes easy to directly output light through the window 12. Here, the phrase "the window 12 is opened" means that no other members are disposed in the window 12.

FIG. 4 is a cross-sectional view of a modification of the device 1 shown in FIG. 3. As shown in FIG. 4, the transparent member 13 allowing transmission therethrough of output light is preferably disposed in the window 12. Consequently, a liquid such as a body fluid can be prevented from entering the shaft 2. In order to improve the effect of preventing liquid entering, it is more preferable to dispose the transparent member 13 over the entirety of the inside of the window 12.

The transparent member 13 preferably has a higher transmissivity than the portion, of the first tubular member 10, in which no window 12 is formed. Regarding materials for forming the transparent member 13, the transparent member 13 can be made from the resin forming the first tubular member 10 or another material that is, for example, a synthetic resin such as a (meth)acrylic resin (for example, polymethyl methacrylate (PMMA)), a polycarbonate resin (for example, poly(diethylene glycol bis(allyl carbonate)) (PC)), a polystyrene-based resin (for example, methyl methacrylate-styrene copolymer resin (MS) or acrylonitrile styrene resin (SAN)), a polyamide resin (for example, nylon), or a polyolefin resin. One type of these materials may be used alone, or two or more types of these materials may be used in combination.

One or more windows 12 can be provided in one first tubular member 10. However, in order to make it easy to adjust the position for irradiation with output light, it is preferable that only one window 12 is provided in one first tubular member 10.

The window 12 is preferably disposed closer to the proximal side than a distal end 10a of the first tubular member 10 is. For example, a distal end 12a of the window 12 can be located within a range of 10 cm from the distal end 10a of the first tubular member 10.

The window 12 is preferably provided at only a part in the circumferential direction of the shaft 2. That is, it is preferable that the window 12 is not provided over the entirety in the circumferential direction of the shaft 2. In particular, the window 12 is preferably located within a range of half the circumference of the shaft 2 and is preferably located within a range of a length, in the circumferential direction of the shaft 2, that is one quarter of the entire circumference of the shaft 2. Consequently, irradiation with output light can be performed selectively in the circumferential direction of the shaft 2.

A length of the window 12 in the longitudinal axis direction of the shaft 2 is preferably larger than a length of the window 12 in the circumferential direction of the shaft 2. Consequently, a treatment site such as a lesion site extending in the longitudinal axis direction of a biological tube wall is easily irradiated.

The window 12 is preferably longer than the cladding-absent portion 24 in the longitudinal axis direction of the shaft 2. Consequently, output light can be applied over a wide range of the window 12 in the longitudinal axis direction of the shaft 2. For the same reason, if a balloon 31 is provided as the expansion portion 30 to the shaft 2, the window 12 is preferably longer than a straight tube portion 33a of the balloon 31 in the longitudinal axis direction of the shaft 2.

A reflection material for refracting, toward the window 12, output light from the core 22 is preferably disposed on the inner surface of the first tubular member 10. The reflection material is more preferably disposed on an inner peripheral wall surface of the first tubular member 10. Examples of a method for disposing the reflection material on the first tubular member 10 include a method in which the inner surface of the first tubular member 10 is coated with a coating agent containing the reflection material. The presence of the reflection material makes it easy to condense output light, whereby irradiation with the output light can be efficiently performed. Examples of a material of the reflection material include aluminum, gold, silver, copper, tin, titanium dioxide, tantalum pentoxide, aluminum oxide, silicon dioxide, magnesium fluoride, and combinations thereof.

FIG. 5 is a perspective view of the entire configuration of the first tubular member 10 shown in FIG. 1. FIG. 6 and FIG. 7 are perspective views of modifications of the first tubular member 10 shown in FIG. 5. As shown in FIG. 5, the first tubular member 10 may be implemented by a resin tube 14 over the entirety thereof in the longitudinal axis direction. Consequently, the first tubular member 10 is easily formed.

Further, as shown in FIG. 6, the first tubular member 10 preferably has a first section 10A provided with a reinforcing material containing a metal. By providing the reinforcing material to the first tubular member 10, torque on the hand side is easily transmitted to the window 12 side. Thus, the position of the window 12 in the circumferential direction is easily adjusted, whereby irradiation that is selective in the circumferential direction is easily performed. The first section 10A preferably extends in the longitudinal axis direction of the first tubular member 10.

The reinforcing material may be formed in the form of a layer or may be obtained by disposing a wire material as a single wire or a stranded wire in a specific pattern, braiding the wire material, or winding the wire material in the form of a coil. Consequently, the strength and torque performance of the shaft 2 can be improved. The first section 10A can be formed by providing the reinforcing material (not shown) on the outer surface or the inner surface of, or in a wall of, the resin tube.

A cross-sectional shape of the wire material forming the reinforcing material may be, for example, any of circular shapes, oblong shapes, polygonal shapes, or shapes obtained by combination thereof. The oblong shapes include an elliptical shape, an oval shape, and a rectangular shape with rounded corners. For materials for forming the reinforcing material, reference can be made to the explanations about the metals for forming the shaft 2. The type of a structural pattern of the reinforcing material is not particularly limited, and the number of turns and the density of the coil are not particularly limited, either. Each of a net-like pattern and the coil may be formed such that the density thereof is unchanging over the entirety in the axis direction or such that the density differs depending on the position in the axis direction.

As shown in FIG. 6, the first section 10A of the first tubular member 10 may be a coil member 15 formed by spirally winding one or more wire materials. Such a first section 10A can be formed as a coreless coil by intertwining a plurality of wire materials. The coil member is preferably a multilayer coil in which a plurality of coils have been stacked. The multilayer coil can be formed by, for example, winding a wire material around a core material to form a first coil and further winding a wire material around the first coil to form a second coil thereon.

As shown in FIG. 6, it is preferable that: the first tubular member 10 further has a second section 10B located closer to the distal side than the first section 10A is, the second section 10B not being provided with the reinforcing material; and the window 12 is located not in the first section 10A but in the second section 10B. The reinforcing material which is present at the first section 10A makes it possible to improve torque-transmission characteristics of the first tubular member 10. Further, since the reinforcing material is not provided to the second section 10B, the window 12 is easily formed in the first tubular member 10. The second section 10B can be implemented by, for example, a resin tube.

As shown in FIG. 7, it is preferable that: the first tubular member 10 further has a third section 10C located closer to the proximal side than the first section 10A is; and the first tubular member 10 is, at the third section 10C, a pipe 16 made from a metal. Consequently, the rigidity of the first tubular member 10 can be gradually improved toward the handle side on the hand side. In order to improve the flexibility of the pipe 16, a plurality of annular grooves or a spiral groove may be formed in the outer surface of the pipe 16. In particular, the groove is preferably formed in the outer surface so as to be closer to the distal side than the center of the pipe 16 in the longitudinal axis direction is.

As shown in FIG. 1, a second handle 62 to be gripped by an operator is preferably connected to the proximal portion of the first tubular member 10. Provision of the second handle 62 makes it easy to perform an operation of moving the first tubular member 10 in the longitudinal axis direction and an operation of rotating the first tubular member 10 about a direction parallel to the longitudinal axis direction of the shaft 2.

As shown in FIG. 5, the first tubular member 10 preferably has, at distal end portions thereof, position indication portions 17 indicating the position of the window 12. Consequently, the position of the window 12 is easily ascertained, whereby a treatment site such as a lesion site can be assuredly irradiated with output light.

Examples of each position indication portion 17 include marks, characters, numerals, symbols, diagrams, and the like. Each mark may be a combination of an axial line extending along the longitudinal axis direction or the circumferential direction of the first tubular member 10 and at least one of a straight line, a curve, or an oblique line intersecting with the axial line, or a point on the axial line.

The position indication portion 17 may be a colored portion on the outer surface of the first tubular member 10 or may be a portion in which a dye such as a pigment has been mixed with the resin forming the first tubular member 10.

One first tubular member 10 may be provided with only one position indication portion 17 or may be provided with a plurality of position indication portions 17.

The position indication portions 17 are preferably provided on both sides of the window 12 in the longitudinal axis direction of the first tubular member 10. Consequently, the position of the window 12 in the longitudinal axis direction of the first tubular member 10 is easily ascertained.

The position indication portions 17 may be provided at positions overlapping with the window 12 in the longitudinal axis direction of the first tubular member 10. Alternatively, the position indication portions 17 may be provided on both sides of the window 12 in the circumferential direction. Consequently, the position of the window 12 in the circumferential direction of the first tubular member 10 is easily ascertained.

As shown in FIG. 2, the light guiding tool 20 preferably includes a second tubular member 26 covering the optical fiber 21 and having light-transmitting property. Consequently, the optical fiber 21 can be reinforced. In addition, it also becomes possible to improve the light diffusing property and reduce unevenness in irradiation. Especially, if a diffusing agent such as titanium oxide is added to a material forming the second tubular member 26, light outputted from the cladding-absent portion 24 is further diffused, whereby unevenness in irradiation can be reduced.

The second tubular member 26 is a tubular member extending in the longitudinal axis direction of the optical fiber 21. In order to protect the optical fiber 21, the second tubular member 26 preferably covers the entirety of the optical fiber 21 in the longitudinal axis direction. Consequently, the entirety of the optical fiber 21 is protected, whereby the core 22 can be inhibited from being damaged, deformed, or bent. For the same reason, the second tubular member 26 preferably covers the entirety of the optical fiber 21 in the circumferential direction. Further, a distal end 26*a* of the second tubular member 26 is preferably located closer to the distal side than the distal end of the optical fiber 21 is, and more preferably located closer to the distal side than the distal end 22*a* of the core 22 is. Consequently, the optical fiber 21 can be prevented from being deformed and damaged at a distal end portion thereof.

The second tubular member 26 only has to have light-transmitting property and is preferably made from a resin. Examples of the resin forming the second tubular member 26 include polyamide-based resins, polyester-based resins, polyurethane-based resins, polyolefin-based resins, fluorine-based resins, vinyl chloride-based resins, silicone-based resins, natural rubber, and the like. Only one type of these resins may be used, or two or more types of these resins may be used in combination. Among these resins, a polyamide-based resin, a polyester-based resin, a polyurethane-based resin, a polyolefin-based resin, or a fluorine-based resin is suitably used.

A material having light diffusing property that is inorganic-based particles such as particles of titanium oxide, particles of barium sulfate, or particles of calcium carbonate, or organic-based particles such as crosslinked acrylic-based particles or crosslinked styrene-based particles, can be added to the resin forming the second tubular member 26.

In order to make it easy to insert the optical fiber 21 into a lumen 27 of the second tubular member 26, the second tubular member 26 preferably has an inner diameter that is unchanging in the longitudinal axis direction of the optical fiber 21.

The outer diameter of the second tubular member 26 is preferably set such that the light guiding tool 20 easily moves in the longitudinal axis direction of the optical fiber 21 inside the lumen 3 of the shaft 2. For example, the outer diameter of the second tubular member 26 may decrease toward the distal end thereof, or the outer diameter may be unchanging in the longitudinal axis direction of the optical fiber 21.

The cladding-absent portion 24 is preferably covered with the second tubular member 26, and the cladding-absent portion 24 is more preferably covered with the second tubular member 26 over the entirety in the longitudinal axis direction of the optical fiber 21. Consequently, a portion of the core 22 corresponding to the cladding-absent portion 24 is protected, whereby the core 22 at the position thereof corresponding to the cladding-absent portion 24 can be inhibited from being damaged, deformed, or bent.

A resin tip (not shown) may be provided at a distal end portion of the second tubular member 26. Consequently, a radioactive ray non-transmitting marker disposed in the lumen 27 of the second tubular member 26 becomes less likely to fall off from a distal end surface side of the light guiding tool 20. The resin tip can be formed in, for example, a hemispheric shape, an elliptical hemispheric shape, a columnar shape, or a prismatic shape. A part of the resin tip is preferably disposed in the lumen 27 of the second tubular member 26. The resin tip preferably has the shape of a plug inserted into the lumen 27 of the second tubular member 26. As a material for forming the resin tip, the same material as the material forming the second tubular member 26 can be used.

As shown in FIG. 1 and FIG. 2, the expansion portion 30 to be expanded radially outward of the shaft 2 is preferably further disposed on the distal portion of the shaft 2. By disposing the expansion portion 30 on the shaft 2, the device 1 is easily fixed to the inside of the body, e.g., a biological tube wall, through expansion of the expansion portion 30. Thus, displacement of the device 1 in the body can be prevented.

FIG. 8 is a cross-sectional view of a modification of the light irradiating medical device 1 shown in FIG. 2. The expansion portion 30 is preferably a balloon, a basket including a plurality of elastic wires, or a stent. The expansion portion 30 is more preferably a balloon, a basket including a plurality of elastic wires, or a self-expandable-type stent. If the expansion portion 30 is a balloon 31, the position in the body can be fixed without damaging a biological tube wall even when the expansion portion 30 comes into contact with the biological tube wall. Meanwhile, if the expansion portion 30 is a basket or a stent 35, a wire material forming the basket or the stent 35 easily bites into a biological tube wall, whereby the device 1 can be firmly fixed to the inside of the body. While FIG. 2 shows an example in which the expansion portion 30 is a balloon 31, FIG. 8 shows an example in which the expansion portion 30 is a stent 35, and FIG. 8 schematically shows the contour of the stent 35.

The balloon 31 may include a distal-side fixed portion 32 fixed to the shaft 2, an inflation portion 33 not fixed to the shaft 2, and a proximal-side fixed portion 34 fixed to the shaft 2 in this order from the distal side. In this case, it is preferable that: the shaft 2 is composed of an inner tube 4 and an outer tube 5; and, at the distal portion of the shaft 2, the inner tube 4 extends out from a distal end of the outer tube 5 and penetrates the balloon 31 in the longitudinal axis direction of the shaft 2. By thus forming the shaft 2 and the balloon 31, the balloon 31 can be joined to the shaft 2.

If the expansion portion 30 is the balloon 31, a fluid supply tool (not shown) is preferably connected to the proximal portion of the shaft 2. The balloon 31 is configured such that a pressure fluid is supplied from the fluid supply tool through the shaft 2 into the balloon 31. The balloon 31 can be expanded by supplying the pressure fluid into the balloon 31. Meanwhile, the balloon 31 can be contracted by drawing out the pressure fluid from inside the balloon 31. When the balloon 31 is expanded, the outer surface of the balloon 31 comes into contact with a biological tube wall of a blood vessel, a gastrointestinal tract, or the like, whereby the shaft 2 can be fixed to the inside of the body.

If the expansion portion 30 is the balloon 31, the shaft 2 may have a plurality of lumens 3. For example, the shaft 2 may have: a first lumen 3*a* into which the first tubular member 10 and the light guiding tool 20 are inserted; and a second lumen 3*b* in communication with the inside of the balloon 31. Consequently, the first lumen 3*a* can be set to function as an insertion path for the light guiding tool 20, and the second lumen 3*b* can be set to function as a flow path for a pressure fluid for expanding and contracting the balloon 31. As shown in FIG. 2, the shaft 2 may be composed of the inner tube 4 and the outer tube 5, the lumen of the inner tube 4 may be the first lumen 3*a*, and the space between the inner tube 4 and the outer tube 5 may be the second lumen 3*b*.

The inflation portion 33 of the balloon 31 may include: the straight tube portion 33*a*; and tapered portions 33*b* respectively formed at the distal portion and the proximal portion of the straight tube portion 33*a*. By bringing the outer surface of the straight tube portion 33*a* of the balloon 31 into contact with a biological tube wall, the shaft 2 can be fixed to the inside of the body.

The balloon 31 is preferably made from a resin. Examples of the resin forming the balloon 31 include polyamide-based resins, polyester-based resins, polyurethane-based resins, polyolefin-based resins, vinyl chloride-based resins, silicone-based resins, natural rubber, and the like. Only one type of these resins may be used, or two or more types of these resins may be used in combination. Among these resins, a polyamide-based resin, a polyester-based resin, or a polyurethane-based resin is suitably used. As these resins, elastomer resins can be used from the viewpoint of the film thickness reduction and the flexibility of the balloon 31.

The type of the fluid to be supplied into the balloon 31 is not particularly limited, and, for example, a liquid such as a physiological saline solution, a contrast agent, or a mixed liquid thereof, or a gas such as air, nitrogen gas, or carbon dioxide, can be used. However, considering transmitting properties for output light, a gas is preferably supplied into the balloon 31.

The basket is formed by banding together a plurality of elastic wires at a first banding portion and a second banding portion that is closer to the proximal side than the first banding portion is. In the basket, the elastic wires are bent or spirally twisted together between the first banding portion and the second banding portion. Although the basket is generally provided to catch an abnormal object such as a calculus, the basket in the present invention is used for fixing the position of the device 1 in the body.

Each elastic wire is a wire material having elasticity and is preferably made from a shape memory alloy or a shape memory resin. The elastic wire may be, for example, a metal wire material that is a single wire or a stranded wire made from a stainless steel such as SUS304 or SUS316, platinum, nickel, cobalt, chromium, titanium, tungsten, aluminum, gold, silver, Ni—Ti alloy, Co—Cr alloy, or the like.

The number of the elastic wires is not particularly limited and can be selected according to the inner diameter of the biological tube wall or the like.

At the first banding portion and the second banding portion, the elastic wires are preferably fixed to the shaft 2. The elastic wires can be fixed to the shaft 2 by methods such as a method in which distal end portions or proximal end portions of the plurality of elastic wires are disposed apart from each other in the circumferential direction of the shaft 2, and the distal end portions or the proximal end portions of the elastic wires are brazed or bonded to the shaft 2 or covered, from above, with a tubular connection tool which is then crimped.

The stent 35 is, for example, a structure that is expandable in diameter and that is formed in a net-like pattern such as a mesh pattern. The stent 35 includes a plurality of struts. The stent 35 can be formed in, for example, a pattern of mutually coupled structural elements extendable and contractable in the circumferential direction and the axis direction. Examples of the type of the stent 35 include: a type in which the stent 35 is in the form of a coil made from one linear metal or macromolecular material; a type in which the stent 35 has been obtained by performing, with a laser or the like, cut-out machining on a metal tube or a tube made from a macromolecular material; a type in which the stent 35 has been assembled by welding linear portions; a type in which the stent 35 has been made by weaving a plurality of linear metals; and the like.

From the viewpoint of an expansion mechanism, the type of the stent 35 can be classified into a balloon-expandable type and a self-expandable type. In the balloon-expandable type, a stent is attached (mounted) on the outer surface of a balloon, transported to a treatment site such as a lesion site, and then expanded at the treatment site by using the balloon. In the self-expandable type, a stent is transported to a lesion site with a catheter having an expansion-inhibiting member, and the expansion-inhibiting member is removed at the treatment site so that the stent expands by itself. The stent 35 provided to the shaft 2 is preferably a self-expandable-type stent. The self-expandable type eliminates the need for providing any balloon inside the stent, and thus the diameter of the stent in a diameter-reduced state can be made smaller than that in the balloon-expandable type.

For materials for forming the stent 35, reference can be made to the explanations about the materials for forming the elastic wires of the basket.

If the expansion portion 30 is a self-expandable-type stent, a proximal end portion of the self-expandable-type stent is preferably fixed to a distal end portion of the shaft 2. Consequently, the device 1 can be fixed to the inside of the body without hindering, by the stent 35, output of light.

If the expansion portion 30 is a self-expandable-type stent and the self-expandable-type stent expands more at a distal end portion thereof than at a proximal end portion thereof, it is preferable that the distal end portion of the self-expandable-type stent is not fixed to the distal end portion of the shaft 2. Consequently, the shaft 2 can be fixed to the inside of the body by bringing the distal end portion of the self-expandable-type stent into contact with a biological tube wall.

The stent 35 can be fixed to the shaft 2 by a method similar to the method for fixing the elastic wires of the basket to the shaft 2. For example, it is possible to employ methods such as a method in which the plurality of struts at the proximal end portion of the stent 35 are disposed apart from each other in the circumferential direction of the shaft 2, and the struts are brazed or bonded to the shaft 2 or proximal end portions of the struts are covered, from above, with a tubular connection tool which is then crimped.

If the expansion portion 30 is a basket or a stent 35, the device 1 preferably further includes a third tubular member (not shown) having a lumen that can accommodate the expansion portion 30. Consequently, a forceps port in an endoscope, the inside of a forceps channel, a tissue in the body other than an abnormal object, and the like can be prevented from being damaged as a result of expansion of the basket or the stent 35 by the time at which the device 1 is transported to near a treatment site such as a lesion site after passing from the forceps port of the endoscope through the inside of the forceps channel.

As shown in FIG. 1 and FIG. 2, the expansion portion 30 may be disposed at a position overlapping with the cladding-absent portion 24 in the longitudinal axis direction of the shaft 2. Alternatively, as shown in FIG. 8, the expansion portion 30 may be disposed closer to the distal side in the longitudinal axis direction of the shaft 2 than the cladding-absent portion 24 is.

If the expansion portion 30 is disposed at a position overlapping with the cladding-absent portion 24 in the longitudinal axis direction of the shaft 2, the expansion portion 30 preferably contains a material having light transmitting property. In this case, it is more preferable that both the expansion portion 30 and a portion of the shaft 2 that is covered with the expansion portion 30 are made from materials having light transmitting property. Consequently, with the cladding-absent portion 24 being positioned inside the expansion portion 30, a target tissue can be efficiently irradiated with light at the position corresponding to the balloon 31. For materials having light transmitting property, reference can be made to the explanations about the shaft 2.

If the expansion portion 30 is disposed at a position overlapping with the cladding-absent portion 24 in the longitudinal axis direction of the shaft 2, the expansion portion 30 preferably contains a material having light diffusing property. In this case, it is more preferable that both the expansion portion 30 and the portion of the shaft 2 that is covered with the expansion portion 30 are made from materials having light diffusing property. By imparting light diffusing property to these portions, a target tissue can be evenly irradiated with light. For materials having light diffusing property, reference can be made to the explanations about the shaft 2.

A support portion 40 supporting the distal portion of the light guiding tool 20 is preferably further disposed on the distal end portion of the shaft 2. Consequently, the distal portion of the light guiding tool 20 can be inhibited from drooping owing to gravity, whereby it becomes easy to perform an operation of rotating the first tubular member 10 and an operation of moving the light guiding tool 20 in the longitudinal axis direction of the shaft 2.

The support portion 40 may be disposed on a radially outer side of the shaft 2 as shown in FIG. 1 and FIG. 2 or may be disposed in the lumen 3 of the shaft 2 as shown in FIG. 8. Further, in order for the support portion 40 to assuredly support the light guiding tool 20, a part of the support portion 40 may be disposed closer to the distal side than the distal end 2a of the shaft 2 is, as in FIG. 1 and FIG. 2.

The support portion 40 can be formed in a tubular shape. As shown in FIG. 8, the tubular support portion 40 may have an inner diameter that is unchanging in the longitudinal axis direction of the shaft 2. Alternatively, as shown in FIG. 1 and FIG. 2, the tubular support portion 40 may have an inner diameter that differs depending on the position in the longitudinal axis direction of the shaft 2. For example, the tubular support portion 40 may include: a large-diameter portion 41 supporting the shaft 2; and a small-diameter portion 42 located closer to the distal side than the large-diameter portion 41 is, the small-diameter portion 42 supporting the light guiding tool 20 and having a smaller inner diameter than the large-diameter portion 41. Consequently, the effect of inhibiting the light guiding tool 20 from drooping owing to gravity can be further improved. For the same reason, the tubular support portion 40 may be formed in a tapered shape such that the inner diameter thereof decreases toward the distal side.

For materials for forming the support portion 40, reference can be made to the explanations about the materials for forming the shaft 2.

If, as shown in FIG. 1 and FIG. 2, the expansion portion 30 is present at the position overlapping with the cladding-absent portion 24 in the longitudinal axis direction of the shaft 2, a distal end 40a of the support portion 40 is preferably located closer to the distal side than a distal end 30a of the expansion portion 30 is. Meanwhile, if, as shown in FIG. 8, the expansion portion 30 is located closer to the distal side in the longitudinal axis direction of the shaft 2 than the cladding-absent portion 24 is, the distal end 40a of the support portion 40 may be located closer to the proximal side than the distal end 30a of the expansion portion 30 is. By thus setting the positional relationship between the expansion portion 30 and the support portion 40, the light guiding tool 20 can be assuredly supported by the support portion 40.

Each of the members composing the light irradiating medical device 1 may be provided with a radioactive ray non-transmitting marker. For example, a first radioactive ray non-transmitting marker 51 may be provided on the distal portion of the shaft 2. Consequently, the position of the shaft 2 can be specified during X-ray fluoroscopy, whereby the position of the shaft 2 can be adjusted to the position of a tissue to be irradiated.

A second radioactive ray non-transmitting marker 52 may be disposed on the second tubular member 26 so as to be closer to the distal side than the distal end of the core 22 is. Consequently, the core 22 is prevented from being deformed or damaged owing to stress generated when the second radioactive ray non-transmitting marker 52 is attached, and the position of the cladding-absent portion 24 which is the light output area of the optical fiber 21 is easily specified during X-ray fluoroscopy.

In addition to the second radioactive ray non-transmitting marker 52, a third radioactive ray non-transmitting marker 53 may be disposed on the second tubular member 26 so as to be closer to the proximal side than a proximal end of the cladding-absent portion 24 is. Consequently, the radioactive ray non-transmitting markers are disposed on both sides, in the longitudinal axis direction of the second tubular member 26, of the cladding-absent portion 24 which is the light output area. Thus, the position of the light output area is more easily specified during X-ray fluoroscopy.

A fourth radioactive ray non-transmitting marker 54 may further be disposed on the shaft 2 so as to be closer to the proximal side than the first radioactive ray non-transmitting marker 51 is. Consequently, the position of the shaft 2 in the longitudinal axis direction is even more easily specified during X-ray fluoroscopy.

A fifth radioactive ray non-transmitting marker 55 is preferably disposed on the distal portion of the first tubular member 10. The fifth radioactive ray non-transmitting marker 55 is more preferably disposed on the said distal portion so as to be closer to the distal side than the window 12 of the first tubular member 10 is. Further, a sixth radioactive ray non-transmitting marker 56 is preferably disposed on the distal portion of the first tubular member 10 so as to be closer to the proximal side than the window 12 is. Consequently, the position of the window 12 in the longitudinal axis direction of the first tubular member 10 is easily ascertained, whereby the position of the light output area is more easily specified during X-ray fluoroscopy.

If the first radioactive ray non-transmitting marker 51, the second radioactive ray non-transmitting marker 52, and the fifth radioactive ray non-transmitting marker 55 are provided to the light irradiating medical device 1, the positions thereof are preferably such that a distal end of the second radioactive ray non-transmitting marker 52, a distal end of the fifth radioactive ray non-transmitting marker 55, and a distal end of the first radioactive ray non-transmitting marker 51 are present in this order from the distal side toward the proximal side. By thus locating the markers, the positions of the shaft 2, the cladding-absent portion 24, and the window 12 are easily ascertained. If the third radioactive ray non-transmitting marker 53, the fourth radioactive ray non-transmitting marker 54, and the sixth radioactive ray non-transmitting marker 56 are provided to the light irradiating medical device 1, the positions thereof are, for the same reason as the above, preferably such that a proximal end of the third radioactive ray non-transmitting marker 53, a proximal end of the sixth radioactive ray non-transmitting marker 56, and a proximal end of the fourth radioactive ray non-transmitting marker 54 are present in this order from the proximal side toward the distal side.

The shape of each radioactive ray non-transmitting marker is not particularly limited and may be, for example, an annular shape or a rod shape. Alternatively, the shape of the radioactive ray non-transmitting marker may be a coil shape or may be a shape having a C-shaped cross section and obtained by forming a slit in a ring. If the shape of the radioactive ray non-transmitting marker is an annular shape or a coil shape, the marker is easily attached to the outer side of the shaft 2, the first tubular member 10, or the second tubular member 26. If the shape of the radioactive ray non-transmitting marker is a rod shape or a coil shape, the marker is easily disposed in the lumen 3 of the shaft 2, the lumen 11 of the first tubular member 10, or the lumen 27 of the second tubular member 26.

The radioactive ray non-transmitting marker is preferably made from, for example, a material containing a metal material such as platinum, gold, silver, tungsten, tantalum, iridium, palladium, or an alloy thereof. The radioactive ray non-transmitting marker may be a metal marker made from the above metal material or may be a resin marker containing the above metal material.

The present application claims the benefit of priority based on Japanese patent application number 2019-150239 filed on Aug. 20, 2019. The entire content of the specification of Japanese patent application number 2019-150239 filed on Aug. 20, 2019 is incorporated herein by reference.

DESCRIPTION OF REFERENCE SIGNS

1 light irradiating medical device
2 shaft
3 lumen
3*a* first lumen
3*b* second lumen
4 inner tube
5 outer tube
10 first tubular member
10A first section
10B second section
10C third section
10*a* distal end of the first tubular member
11 lumen
12 window
13 transparent member
14 resin tube
15 coil member
16 pipe
17 position indication portion
20 light guiding tool
21 optical fiber
22 core
22*a* distal end of the core
23 cladding

24 cladding-absent portion
25 connector
26 second tubular member
26*a* distal end of the second tubular member
30 expansion portion
31 balloon
32 distal-side fixed portion
33 inflation portion
33*a* straight tube portion
33*b* tapered portion
34 proximal-side fixed portion
35 stent
40 support portion
41 large-diameter portion
42 small-diameter portion
51 first radioactive ray non-transmitting marker
52 second radioactive ray non-transmitting marker
53 third radioactive ray non-transmitting marker
54 fourth radioactive ray non-transmitting marker
55 fifth radioactive ray non-transmitting marker
56 sixth radioactive ray non-transmitting marker
61 first handle
62 second handle

The invention claimed is:

1. A light irradiating medical device comprising:

a shaft having a first end and a second end in a longitudinal axis direction thereof and having a lumen extending in the longitudinal axis direction from a proximal side toward a distal side;

a first tubular member disposed in the lumen of the shaft and rotatable about a rotation axis parallel to the longitudinal axis direction of the shaft, the first tubular member having a window on the first tubular member located in a part of a peripheral wall of a distal portion; and a light guiding tool disposed in a lumen of the first tubular member and movable in the longitudinal axis direction, the light guiding tool including an optical fiber extending in the longitudinal axis direction, the optical fiber including
a core,
a cladding coating a radially outer portion of the core, and
a cladding-absent portion located at a part of a distal portion of the core, and the first tubular member and the light guiding tool being configured so that a light emitted from the optical fiber is allowed to pass through the window, wherein the light guiding tool includes a second tubular member covering the optical fiber wherein the second tubular member has a light-transmitting property, the second tubular member extends in the longitudinal axis direction and is disposed in the lumen of the first tubular member so that the second tubular member longitudinally covers an entirety of the optical fiber in the longitudinal axis direction, and the cladding-absent portion is a portion which has a length in a longitudinal direction of the optical fiber and in which the core is exposed.

2. The light irradiating medical device according to claim 1, wherein the first tubular member comprises a material having a lower transparency than the window so that the first tubular member allows the light emitted from the light guiding tool to pass therethrough less than the window.

3. The light irradiating medical device according to claim 1, further comprising a transparent member disposed at the window, the transparent member allowing the light emitted from the light guiding tool to pass through the window.

4. The light irradiating medical device according to claim 1, wherein the window has a length of the window in the longitudinal axis direction of the shaft and a width in a circumferential direction of the shaft, and the length is larger than the width.

5. The light irradiating medical device according to claim 1, wherein the window is located within a range of a length, in a circumferential direction of the shaft, that is one quarter of an entire circumference of the shaft.

6. The light irradiating medical device according to claim 1, further comprising an expansion portion disposed on a distal portion of the shaft and configured to expand radially outward of the shaft.

7. The light irradiating medical device according to claim 6, wherein the expansion portion is at least one selected from the group consisting of a balloon, a basket including a plurality of elastic wires, and a self-expandable stent.

8. The light irradiating medical device according to claim 1, wherein the first tubular member has a first section provided with a reinforcing material containing a metal.

9. The light irradiating medical device according to claim 8, wherein the first tubular member further has a second section located closer to a distal side than the first section is, the second section not being provided with the reinforcing material, and the window is located not in the first section but in the second section.

10. The light irradiating medical device according to claim 8, wherein the first tubular member further has a third section located closer to a proximal side than the first section is, and the third section of the first tubular member comprises a pipe made from a metal.

11. The light irradiating medical device according to claim 1, further comprising a support portion disposed on a distal end portion of the shaft and supporting a distal portion of the light guiding tool.

12. The light irradiating medical device according to claim 1, wherein the window is longer than the cladding-absent portion in the longitudinal axis direction of the shaft.

13. The light irradiating medical device according to claim 1, further comprising a reflection material disposed on an inner surface of the first tubular member and configured to refract, toward the window, a light emitted from the core of the optical fiber.

14. The light irradiating medical device according to claim 1, wherein the first tubular member has, at a distal end portion thereof, a position indication portion indicating a position of the window.

15. The light irradiating medical device according to claim 1, wherein the light guiding tool and the shaft are configured so that the light guiding tool is not rotated, relative to the shaft, about an axis parallel to the longitudinal axis direction of the shaft.

16. The light irradiating medical device according to claim 1, wherein the second tubular member is configured such that a distal end of the second tubular member further passes a distal end of the shaft toward the distal side.

* * * * *